United States Patent [19]

Martinez et al.

[11] Patent Number: 4,645,645

[45] Date of Patent: Feb. 24, 1987

[54] OXYGENATOR HAVING AN IMPROVED HEAT EXCHANGER

[75] Inventors: Felix J. Martinez, Plymouth; Larry E. Fuller, Minnetonka; Richard J. Irmiter, Minneapolis, all of Minn.

[73] Assignee: Renal Systems, Inc., Minneapolis, Minn.

[21] Appl. No.: 719,999

[22] Filed: Apr. 4, 1985

[51] Int. Cl.$^4$ .............................. A61M 1/16
[52] U.S. Cl. ..................... 422/46; 165/163; 165/184; 210/321.4; 422/48
[58] Field of Search ..................... 422/46-48; 210/321.3, 321.4; 165/160, 161, 163, 179, 181, 175

[56] References Cited

U.S. PATENT DOCUMENTS

| | | | |
|---|---|---|---|
| 2,181,927 | 12/1939 | Townsend | 165/181 |
| 3,202,210 | 8/1965 | Hughes | 165/179 |
| 3,468,631 | 9/1969 | Raible et al. | 23/258.5 |
| 3,488,158 | 1/1970 | Bentley | 23/285.5 |
| 3,508,662 | 4/1970 | Miller, III | 210/321 |
| 3,595,310 | 7/1971 | Burne et al. | 165/181 |
| 4,058,369 | 11/1977 | Bentley | 23/285.5 B |
| 4,065,264 | 12/1977 | Lewin | 23/258.5 |
| 4,138,464 | 2/1979 | Lewin | 422/46 |
| 4,182,739 | 1/1980 | Curtis | 422/47 |
| 4,196,075 | 4/1980 | Bentley | 210/19 |
| 4,248,828 | 2/1981 | Bentley | 422/47 |
| 4,268,476 | 5/1981 | Raible | 422/46 |
| 4,297,318 | 10/1981 | Raible | 422/46 |
| 4,374,088 | 2/1983 | Stenberg et al. | 422/46 |
| 4,376,095 | 3/1983 | Hasegawa | 422/46 |
| 4,412,190 | 1/1984 | Mather, III | 422/46 |
| 4,428,180 | 1/1984 | Raible | 56/11.3 |
| 4,495,989 | 1/1985 | Sievers | 165/172 |

OTHER PUBLICATIONS

William Harvey HF-4000 Series Oxygenator.
Bentley BOS-CM40 Series, 1983, 1984.
COBE CML brochure.
Terumo Capiox II brochure.
Bentley BOSCM 40 and BOS CM50 Capillary Fiber Membrane Oxygenators Product Bulletin-1984 and 1984.

Primary Examiner—Michael S. Marcus
Attorney, Agent, or Firm—Vidas & Arrett

[57] ABSTRACT

A hollow fiber type blood oxygenator having an integrated and improved heat exchanger having a generally conical housing and core member between which a helically wrapped conduit is situated. The conduit has a plurality of parallel flutes. A housing and core member are formed with helical recessed regions which conform to the conical helix defined by the tubing or conduit. The tubing is formed with flattened opposing surfaces which mate with the corresponding recesses in the housing and core member. The mating on the flats on the tube or conduit to the corresponding flats in the recessed regions of the housing and core member allows a substantially tighter and more uniform fit which minimizes the dynamic blood priming volume.

3 Claims, 3 Drawing Figures

OXYGENATOR HAVING AN IMPROVED HEAT EXCHANGER

DESCRIPTION

1. Field of the Invention

This invention relates to a hollow fiber type gas exchanger commonly referred to as an artificial lung or oxygenator having an integrated and improved heat exchanger.

2. Description of the Prior Art

During open heart surgery a portion of a patient's blood is circulated extracorporeally for gas exchange by means of an artificial lung or oxygenator. Blood usually loses heat within the extracorporeal circuit and requires warming to the patient's body temperature by means of a heat exchanger. The heat exchanger may also be used for cooling the circulating blood when a lower than normal body temperature is desired.

Hollow fiber type artificial lungs such as shown in U.S. Pat. No. 4,376,095 which issued Mar. 8, 1983 to Hasegewa include an oxygenator section comprised of a plurality of hollow fiber type tubules and a heat exchanger section having a plurality of tubes aligned in a side by side manner.

Blood oxygenators having integral heat exchangers having also been provided in which the heat exchanger includes a tube having an integral, substantially continuous helical rib along its length which provides a substantially continuous helical fluid path. The tube is positioned within a chamber which is connected to the extracorporeal blood circuit. Such designs are typified by U.S. Pat. No. 4,138,464 which issued Feb. 6, 1979 to Lewin.

The oxygenator sold by American Bentley, a subsidiary of American Hospital Supply Corporation of Irvine, Calif. under its designation "BOS-CM Series" includes an oxygenator portion comprised of a hollow fiber type oxygenator and a heat exchanger section in which a round heat exchanger conduit of circular cross-section is helically wrapped around an inner core, both of which are surrounded by a housing which includes a helical recess to match the heat exchanger conduit helix. The heat exchanger conduit includes a plurality of concentric ring shaped ridges to increase the surface area of the heat exchanger tube which is exposed to the circulating blood. The ring shaped ridges create a surface area of approximately four square inches per linear inch of tube.

The Bentley BOS-CM series oxygenators combines some of the advantages of the heat exchanger of Lewin U.S. Pat. No. 4,138,464 with the oxygenator of Hasegewa, U.S. Pat. No. 4,376,095. However, the dynamic priming volume of the heat exchanger of the Bentley oxygenator is quite high due to the large volume of wasted space between the heat exchanger conduit, the core and the outer housing. One of the objects of the present invention is to reduce the priming volume of the heat exchanger portion of a hollow fiber membrane oxygenator having an intregal heat exchanger.

BRIEF SUMMARY OF THE INVENTION

The apparatus of the present invention consists of an oxygenator having a gas exchanger section and a heat exchanger section. The gas exchanger section consists of a plurality of microporous hollow fibers which are encapsulated at both ends with potting compound. The potting compound is cut in a fashion so as to open the ends of the fibers to blood flow. The fiber bundle is preferably contained within a clear housing. The teachings of Hasegewa U.S. Pat. No. 4,376,095 show the details of a hollow fiber oxygenator and is hereby incorporated by reference as an example of a suitable example of an oxygenator section.

The heat exchanger section consists of a housing which defines a heat exchanger chamber when connected to the gas exchanger section. The housing is generally conical in shape with the largest diameter of the cone being attached to the gas exchanger section. A cone shaped core member having sealed ends is positioned within the conical housing. A coated tubing preferably anodized aluminum having a plurality of parallel flutes or ridges is coiled helically around the sealed core member within the housing.

Both the housing and core member are formed with helical recess regions which conform to the conical helix defined by the tubing or conduit. It has been found that fluted tubing formed with flattened opposing surfaces which mate with the corresponding recesses in the housing and core member will decrease the priming volume of the heat exchanger. The mating of the flats on the tube to the corresponding flats in the recess regions of the housing and core member allows a substantially tighter and more uniform fit. Such a construction provides a dynamic priming volume which is approximately ½ less than the volume required when a heat exchanger tube of fluted circular cross section is utilized. Also, the blood path thickness is minimized which increases the heat exchanger efficiency.

BRIEF DESCRIPTION OF THE DRAWINGS

A detailed description of one preferred embodiment of the invention is hereafter described with specific reference being made to the drawings in which.

DETAILED DESCRIPTION OF THE INVENTION

Figure 1:
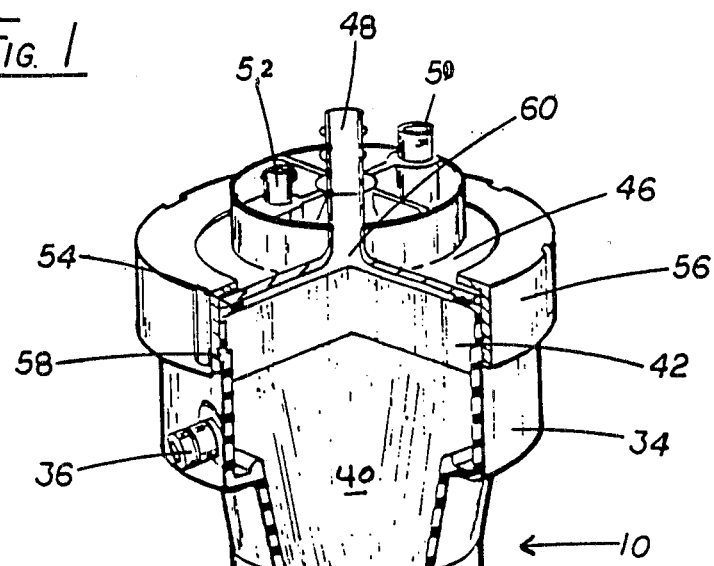
FIG. 1 is a vertical elevational partial sectional view of a oxygenator having an intregal heat exchanger constructed in accordance with the present invention with parts cut away to the show the gas exchanger and heat exchanger sections.
Figure 2:
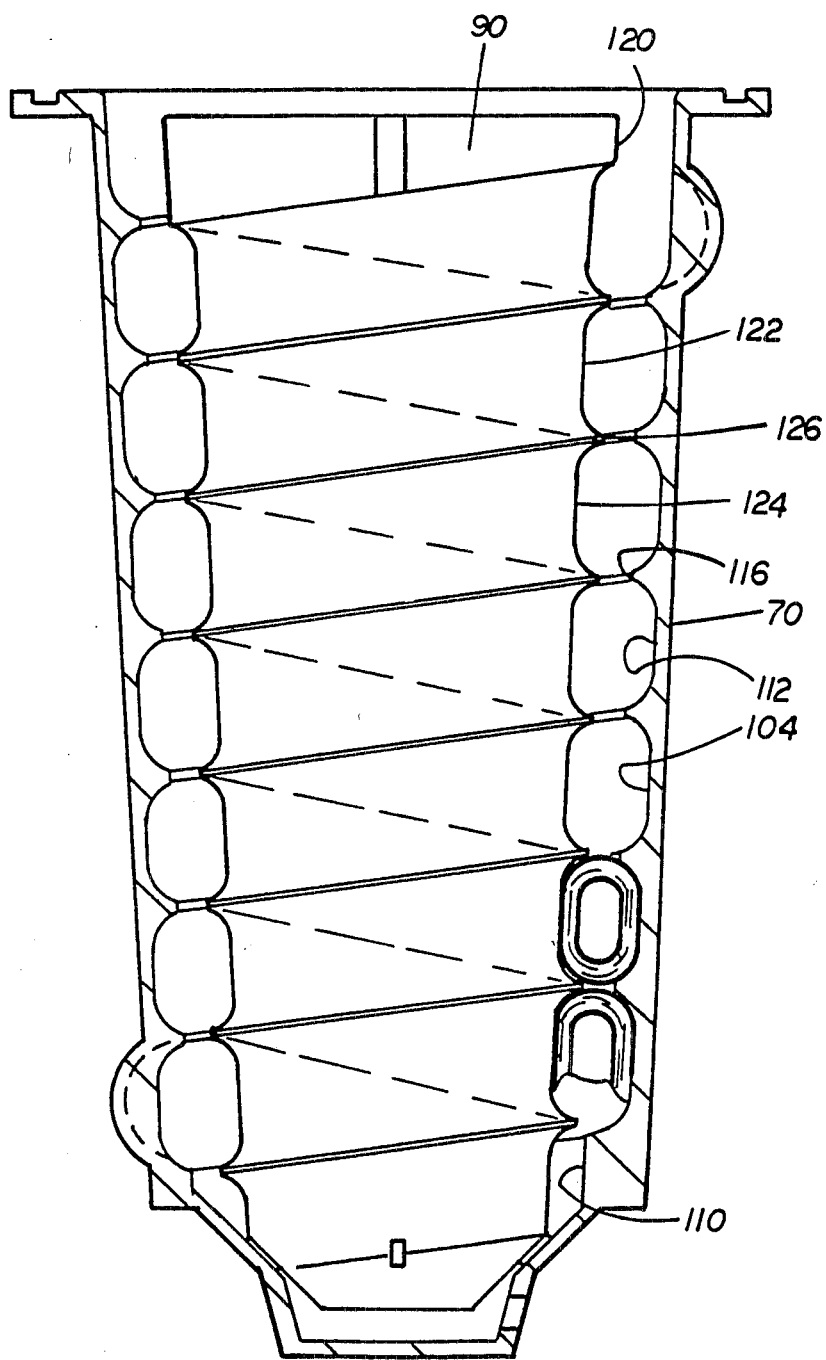
FIG. 2 is an vertical elevational view of the heat exchanger section of FIG. 1 showing the heat exchanger conduit and housing in cross-section.

Referring to FIGS. 1 and 2, the hollow fiber type oxygenator having an enclosed heat exchanger section according to the present invention comprises a hollow fiber gas exchanger section 10 and a heat exchanger section 20 which are integrally connected to each other by means of head nut 30.

The gas exchanger section 10 has a housing formed from a tubular main body 34 which is preferably formed of a clear plastic material and optionally may include internal ribs. A gas inlet 36 and gas outlet 38 are provided on housing 34 as shown.

A bundle of separate hollow fibers 40 are arranged within housing 34 parallel to the longitudinal axis of the housing 34. The ends of the hollow fibers 40 are open and are retained in liquid tight manner by walls 42, 44. The walls are prepared by having a polymeric potting agent poured onto the inner wall surfaces on either end of the housing. After the poured potting agent has encapsulated the ends of fibers 40 and hardened, the hardened resin is cut to expose the open ends of the hollow fibers 40 which completes the preparation of the walls 42, 44. Hollow fiber construction and encapsulation of the ends thereof are disclosed, for example, fiber construction and the blood oxygenator 10 are taught in U.S. Pat. No. 4,376,095 to Hasagawa. The internal construction details of the blood oxygenator section do not form a part of the present invention.

The upper end of the oxygenator section 10 includes a header 46 which defines a blood outlet 48, a temperature probe port 50 and sampling port 52. An O-ring gasket 54, which is preferably formed of low Durometer elastomer is positioned between header 46 and main body 34 in order to form a fluid tight seal. A plastic head nut 56 is threaded over header 46 onto matching threads 58 of main body 34. Blood which exits hollow fibers 40 enters space 60 formed between wall 42 and header 46 and then leaves via tube 48.

The heat exchanger section 20 includes a generally conically shaped heat exchanger housing 70 which is preferably formed of clear plastic material in order to allow visual inspection of blood therewithin. An O-ring 72 forms a liquid tight seal between the interior of housing 70 and oxygenator 10. A plastic header nut 30 is threaded on housing 70 as shown in FIGS. 1 and 2 to provide a seal and to hold the gas exchanger and heat exchanger sections of the oxygenator together.

Housing 70 includes a blood inlet port 74 which introduces venous blood into the heat exchanger section 20. A temperature probe port 76 enters the housing horizontally at its extreme lower end so as to minimize any dead space. Heat exchanger fluid inlet 78 and outlet 80 penetrate housing 70 as shown to allow the introduction of water or other heat exchange media into the heat exchanger.

A heat exchanger core 90 formed from a suitably biocompatible material such as ABS of polypropylene is conically shaped and is preferably colored white so as to provide a contrast with the blood which will be in the heat exchanger section. Preferably, heat exchanger core 90 is hollow and is closed at each end.

Figure 3:
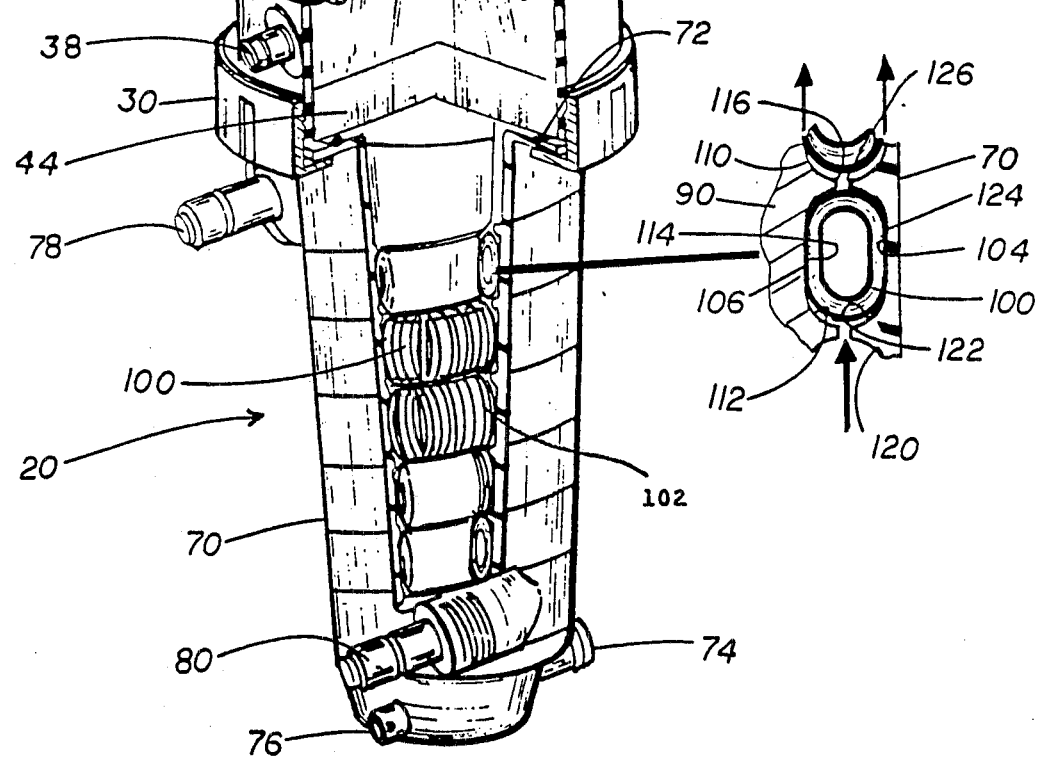
FIG. 3 is an enlarged partial sectional view of the heat exchanger conduit, core and housing taken along lines 3—3 of FIG. 1.

The heat exchanger or conduit 100 is formed of a thin walled tube of high heat conducting metal. Conduit 100 is formed with a plurality of parallel flutes or ribs 102 throughout the length of conduit 100 as shown in FIGS. 2 and 3. The entire conduit or tubing is suitably coated to provide biocompatability with human blood. Suitable anodized, fluted tubing is available from Turbotech Products, Inc. of Windsor, Conn. The aluminum conduit available from Turbotech Products employed in this invention had an initial circular cross-section and a diameter of about 0.73 inches (1.85 cm).

Heat exchanger conduit 100 is formed with two opposing flattened surfaces 104 and 106 as shown in FIGS. 2 and 3. The conduit may either be formed initially having flattened surfaces or may be formed from a tube which originally had a circular cross-section.

When a 0.730 inches (1.85 cm) diameter aluminum fluid conduit was employed by the inventors, it was flattened until the distance between opposing flattened surfaces 104 and 106 was 0.540 inches plus or minus 0.015 inches (1.37±0.04 cm). It was found that a round tube could not be flattened to less than about 0.50 inches (1.27 cm) in diameter across the flats because the aluminum would develop cracks. However, the tubing may be originally formed having flattened opposing surfaces, rather than starting with conduit having a circular cross-section, which would then allow a minimum diameter of less than 0.50 inches (1.27 cm). Generally, if X is equal to the diameter of the round tubing, it should be flattened until the minimum diameter across the flats is between about 0.72X and 0.76X.

Heat exchanger conduit 100 is then formed into a conical helix such that opposing flattened surfaces 104 all face the outside and opposing flattened surfaces 106 face the inside of the cone defined by the conical helix. All of the flats define a line which is preferably about 2 degrees, 52 minutes off from the vertical axis defined by the helix.

Housing 70 includes an inner wall 110 which is configured to define conical helical recess region 112 which conforms to the helix defined by the helical conduit 100. The helical recess region 112 includes flats 114 and peaks 116 between adjacent flats 114 of the helix. The top of peak 116 is preferably slightly radiused as shown in FIG. 3 such that it does not present a sharp edge which may be broken by contact with conduit 100.

It has been found that the heat exchanger construction wherein the housing has flats 114 which correspond to flattened surface 104 of conduit 100 allows the production of a heat exchanger section which will have both high heat exchange efficiency and a low dynamic priming volume. The relatively long flats 114 and 104 allow peaks 116 to be relatively shallow. As peaks 116 are made longer, they become thinner and are more likely to break off fragments when a helical conduit contacts the relatively fragile peaks. A helical recess region configured to match the shape of a conduit having circular cross-sectional would require very high, thin peaks in order to maximize the area of contact between the conduit and housing in order to minimize the priming volume. Such a construction would be too fragile and would result in the breakage of numerous ridge peaks which would defeat the purposes of such a construction.

Heat exchanger core 90 includes an external surface 120 which also includes a conical helical recess region 122 configured to conform to the helical conduit 100. Helical recess region 122 includes flats 124 and peaks 126 constructed and arranged as described above for the helical recess region of the housing.

Helical conduit 100 is placed within housing 110 such that the conduit ends pass through the housing and form heat exchanger fluid inlet 78 and outlet 80. The conical helical shaped core 90 is then screwed into position. The cone shape provides a tight fit between the core, conduit and housing when the core reaches the bottom of the housing. The flattened surfaces 104 of the conduit are held closely to flats 114 of housing 110. Ribs or flutes 102 allow fluid flow from one flat to the next and so forth. Likewise, flattened surfaces 102 of conduit 100 are closely held to flats 124 of the heat exchanger core 90. As a result, the dynamic priming volume of the heat exchanger section is considerably reduced from previously known oxygenators having heat exchanging sections. As an example, the heat exchanger section constructed in accordance with the invention requires about 210 cc of blood for priming. In contrast, a Bentley BOS-CM heat exchanging section of substantially similar size requires about 340 cc of blood for priming. The use of the present inventions matching flat recesses and flat conduit surfaces results in about 38% decrease in priming volume while maintaining optimal heat exchanging characteristics.

The heat exchanger fluid inlets and outlets 78 and 80 form a fluid tight connection with the open ends of conduit 100. Preferably, inlet 78 and outlet 80 are fabricated for connection with a quick-disconnect water supply. Likewise, gas inlet 36 and gas outlet 38 are preferably constructed with a quick-connect type fitting so as to allow ready connection to oxygen lines.

In considering this invention, it should be remembered that the disclosure is illustrative only and that the scope of the invention is to be determined by the appended claims.

What is claimed is:

1. In a hollow fiber-type oxygenator having an enclosed heat exchanger section and gas exchanger section, said gas exchanger section comprising a first housing, a bundle of a multiplicity of hollow fibers for gas exchange, said hollow fibers being physically separated from one another and arranged side by side within said first housing, first and second wall portions liquid-tightly supporting said hollow fibers at the opposite end portions of said hollow fibers so that the ends thereof are left open, said first and second walls defining with said fibers a blood chamber and a gas exchanger, gas exchanger inlet and outlet means communicating with said gas exchanger chamber, and a first blood circulation opening in said housing providing communication with said blood chamber, the improvement comprising;
    (a) a heat exchanger section including second housing means in fluid tight communication with the end portions of said gas exchanger section adjacent said second wall, said second housing means having an interior and exterior;
    (b) a heat transfer fluid conduit having a cross-sectional configuration of at least two planar substantially parallel opposing walls, said conduit including heat exchange fluid inlet and outlet means, said conduit being wound in a helix within said second housing means said helix and said heat exchange inlet and outlet means providing fluid communication through said conduit to the exterior of said second housing means;
    (c) heat exchanger section core means within said second housing means arranged such that said conduit is helically surrounding and in contact with said core means substantially along the entire length of said conduit;
    (d) said conduit further including a rib means along its length, said rib means comprising a plurality of parallel ribs about the external circumference of said conduit so as to increase the heat exchange surface area of said conduit; the cross-section of the conduit and rib means defining extended substantially planar surface regions which are generally parallel to a line drawn through centers of said conduit that form adjacent loops of said conduit
    (e) said second housing means including an inner wall surface configured to define a helical recess region conforming to the helical conduit throughout its length such that the outer planar surface of the conduit and inner wall recess regions cooperate to define a low volume channel through which blood may pass from a blood inlet means in fluid tight communication with the interior of said second housing means to said gas exchanger section; and
    (f) said core means including an external wall surface configured to define a helical recess region conforming to the helical conduit such that the inner planar surface of the conduit and external wall recess region provide a low volume channel through which blood may pass from said blood inlet means to said gas exchanger section.

2. In a blood oxygenator having an integral heat exchanger for regulating the temperature of the blood flowing in an extracorporeal blood circuit, comprising a gas exchanger section comprised of a first housing; a bundle of a multiplicity of hollow fibers for gas exchange, said hollow fibers arranged side by side within said first housing; first and second walls liquid-tightly carrying said hollow fibers at the end portions of said hollow fibers, with the end portions of said hollow fibers being left open, said first and second walls defining a gas exchange chamber with the inner wall of said first housing and outer wall surfaces of said hollow fibers; oxygen inlet and outlet means communicating with said gas exchange chamber; and a first blood circulation opening communicating with an interstitial space of said hollow fibers externally of said first wall; the improvement comprising a heat exchanger section comprising:
    (a) a second housing defining a heat exchanger chamber with the second wall of said gas exchanger section such that said second housing is in fluid communication with the interior of said hollow fibers;
    (b) heat transfer fluid conduit means for carrying heat exchange fluid, said conduit means including a conduit having a plurality of rib members about its circumference, each of said rib members being parallel to each other, said conduit being wrapped in a conical helix defining an interior and exterior of a cone and said conduit having flattened surfaces on the interior and exterior of the cone defined by said conduit, said flattened surfaces such that if the diameter of round conduit is equal to x, the minimum diameter across the flats of said conduit is $(0.74 \pm 0.02)X$;
    (c) heat exchanger section core means within said second housing, said core means being conical in shape and being configured with an exterior surface which defines a helical recess region including flattened surfaces conforming to the helix of said flattened conduit such that said conduit may be tightly wrapped about said core thereby defining a low volume channel through which blood may pass between the recess regions and adjacent conduit; and
    (d) said second housing having an internal wall being conical in shape and configured such that its inner surface defines a helical recess region including flattened surfaces conforming to the helix of said flattened conduit such that when said core means and conduit are positioned therewithin a low volume channel is defined between said housing recess regions and said conduit through which blood may pass from a blood inlet means in fluid communication with the interior of said second housing to the interior of said hollow fibers.

3. In a blood oxygenator having an integral heat exchanger for regulating the blood temperature, said oxygenator including a gas exchanger section comprising a hollow fiber oxygenator in which the blood inlet to the fiber oxygenator is joined in fluid tight relation to a heat exchanger section, the improvement comprising a heat exchanger section comprising:
    (a) a housing defining a heat exchanger chamber with the blood inlet of the fiber oxygenator such that said chamber is in fluid communication with the interior of said hollow fibers, said housing further including blood inlet means for carrying blood to be oxygenated therewithin;

(b) heat transfer fluid conduit means for carrying heat exchange fluid, said conduit means including a conduit having a plurality of concentric rib members about its circumference, said conduit being wrapped in a conical helix defining an interior and exterior of a cone, the conduit having flattened opposing surfaces on the interior and exterior of the cone defined by said helix;

(c) heat exchanger core means within said housing, said core means being conical in shape and being configured having an exterior surface which defines a helical recess region conforming to the helix of said flattened conduit so as to minimize fluid volume therebetween; and (d) said housing having an internal wall being conical in shape and being configured such that its inner surface defines a helical recess region conforming to the helix of the flattened conduit such that said conduit is tightly wrapped between said core means and housing to thereby minimize the volume of the channels through which blood may pass between the recess regions and conduit.

* * * * *